United States Patent
Ruedinger et al.

(10) Patent No.: US 6,274,763 B1
(45) Date of Patent: Aug. 14, 2001

(54) SHELL CATALYST FOR PRODUCING ACETIC ACID BY GAS PHASE OXIDATION OF UNSATURATED $C_4$-HYDROCARBONS

(75) Inventors: Christoph Ruedinger; Hans-Juergen Eberle; Norbert Zeitler; Max Wollin; Gudrun Wittmann, all of München (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/308,213

(22) PCT Filed: Nov. 27, 1997

(86) PCT No.: PCT/EP97/06612
§ 371 Date: May 14, 1999
§ 102(e) Date: May 14, 1999

(87) PCT Pub. No.: WO98/23371
PCT Pub. Date: Jun. 4, 1998

(30) Foreign Application Priority Data

Nov. 28, 1996 (DE) .............................................. 196 49 426

(51) Int. Cl.[7] ..................................................... C07C 51/25
(52) U.S. Cl. .......................... 562/548; 562/607; 502/303; 502/304; 502/349; 502/353
(58) Field of Search ................................... 562/548, 607; 502/303, 304, 349, 353

(56) References Cited

U.S. PATENT DOCUMENTS

| | | |
|---|---|---|
| 3,509,179 | 4/1970 | Friedrichsen et al. . |
| 3,917,682 | 11/1975 | Mizukami et al. . |
| 3,948,807 | * 4/1976 | Fuchigami et al. . |
| 3,954,857 | 5/1976 | Brockhaus . |
| 4,113,660 | * 9/1978 | Abe et al. . |
| 4,146,734 | 3/1979 | Slinkard . |
| 4,324,694 | 4/1982 | Reuter et al. . |
| 4,448,897 | 5/1984 | Gastinger . |
| 5,493,052 | 2/1996 | Tenten et al. . |
| 5,677,261 | 10/1997 | Tenten et al. . |

FOREIGN PATENT DOCUMENTS

| | | |
|---|---|---|
| 1279011 | 10/1968 | (DE) . |
| 1442590 | 10/1968 | (DE) . |
| 2026744 | 4/1971 | (DE) . |
| 2016681 | 10/1971 | (DE) . |
| 2110876 | 10/1971 | (DE) . |
| 2354425 | 5/1975 | (DE) . |
| 4442346 | 5/1996 | (DE) . |
| 0021325 | 1/1981 | (EP) . |
| 0609750 | 8/1994 | (EP) . |
| 1165442 | 10/1969 | (GB) . |
| 1333306 | 10/1973 | (GB) . |
| 1 446 323 | * 8/1976 | (GB) . |

OTHER PUBLICATIONS

Derwent Abstract (#74–11613V [07] ) corresponding to DE 2235103.
Derwent Abstract (#71–674715 [42] ) corresponding to DE 2016681.

* cited by examiner

Primary Examiner—Paul J. Killos
Assistant Examiner—Robert W. Deemie
(74) Attorney, Agent, or Firm—Collard & Roe, P.C.

(57) ABSTRACT

The invention relates to a shell catalyst for producing acetic acid by gas-phase oxidation of unsaturated $C_4$-hydrocarbons, comprising an inert non-porous carrier and a catalytically active mixed oxide material applied on the outer surface of the carrier, wherein said material contains (a) one or several oxides from the group titanium dioxide, zircon dioxide, stannic dioxide, aluminum oxide, and b) 0.1 to 1.5 wt. % vanadium pentoxide in relation to the weight of the constituent (a) and per $m^2/g$ of the specific surface of the constituent (a).

8 Claims, No Drawings

SHELL CATALYST FOR PRODUCING ACETIC ACID BY GAS PHASE OXIDATION OF UNSATURATED $C_4$-HYDROCARBONS

The invention relates to a coated catalyst for preparing acetic acid by gas-phase oxidation of unsaturated $C_4$-hydrocarbons, and also a process for preparing acetic acid by gas-phase oxidation of unsaturated $C_4$-hydrocarbons using the coated catalyst.

It is known that acetic acid can be prepared by gas-phase oxidation of $C_2$-, $C_3$- and $C_4$-molecules by means of a catalyst. However, up to now it has not been possible to find a process which is economical and fully satisfactory in terms of operability.

DE-B 1279011 describes a process for preparing acetic acid by catalytic gas-phase oxidation of butene with oxygen using aluminium vanadate and titanium vanadate catalysts. These catalysts are prepared by precipitating the mixed oxides from the corresponding solutions, with the mixed oxides being able to be mixed, if desired, with inert materials such as silica. The catalyst is used as a finely divided powder in fluidized-bed reactors. A disadvantage of such uniform-composition catalysts is the high degree of total oxidation.

To improve the yield of such catalysts, DE-A 2016681 proposes pretreating the catalysts with an oxidizing agent prior to calcination. DE-A 2354425 (U.S. Pat. No. 3,954, 857) proposes treating the calcined titanium-vanadium mixed catalyst with hydrochloric acid to improve the selectivity. The catalysts are used as uniform-composition catalysts, if desired in admixture with inert support materials such as silica.

A further starting point known from the prior art for improving the activity of titanium-vanadium mixed catalysts in the gas-phase oxidation of butenes to acetic acid is the use of $TiO_2$ in a defined crystal form or with a defined surface area. DE-A 2026744 (U.S. Pat. No. 3,917,682) describes Ti-V mixed catalysts whose $TiO_2$ component is predominantly present as rutile. The catalysts can be used in powder form or after pressing into shaped bodies. U.S. Pat. No. 4,448,897 discloses Ti-V catalysts for butene oxidation which contain $TiO_2$ having a BET surface area of greater than 40 $m^2/g$. The catalysts are likewise used in powder form or as pressed compacts.

It is also known from the prior art that the selectivity of Ti-V catalysts in butene oxidation can be improved by completely or partially replacing the titanium dioxide by other metal oxides. DE-A 2110876 (GB-A 1333306), for example, describes catalysts which contain oxides of molybdenum, tin and vanadium as active components. The catalysts are used in powder form and the mixed oxide catalyst can, if desired, also be applied to finely divided support materials such as silicon dioxide. U.S. Pat. No. 4,146,734 discloses the use of vanadium mixed oxides which are doped with cerium and further transition metal oxides. The catalyst is used as a finely divided granular material, but can also be applied as precipitate to finely divided, inert supports.

DE-A 2235103 discloses Ti-V mixed oxide catalysts for the gas-phase oxidation of butenes in the form of supported catalysts prepared by impregnating a preformed porous support with the mixed solution of the catalyst components.

In all these processes, the catalysts used are uniform-composition catalysts in which the active components themselves are used as powder or compacts, or diluted with finely divided support materials as powder or compacts. Porous supports impregnated throughout with active component as described in DE-A 2235103 are also to be regarded as uniform-composition catalysts since here too the entire catalyst volume is catalytically active. Disadvantages of uniform-composition catalysts are the high degree of total oxidation and the difficulty of controlling the butene oxidation at high conversions.

It is therefore an object of the invention to provide a catalyst and a process for preparing acetic acid by gas-phase oxidation of unsaturated $C_4$-hydrocarbons, which catalyst and process lead to a better yield and better operability in the oxidation reaction.

It has been found that coated catalysts in which the active composition is applied as a thin layer to a nonporous support body are particularly suitable for preparing acetic acid by gas-phase oxidation of unsaturated hydrocarbons having four carbon atoms.

The invention provides a coated catalyst for preparing acetic acid by gas-phase oxidation of unsaturated $C_4$-hydrocarbons which consists of an inert nonporous support body and a catalytically active mixed oxide composition which is applied to the outer surface of the support body and contains a) one or more oxides selected from the group consisting of titanium dioxide, zirconium dioxide, tin dioxide, aluminium oxide and b) from 0.1 to 1.5% by weight, based on the weight of the component a) and per $m^2/g$ of specific surface area of the component a), of vanadium pentoxide.

Here, % by weight based on the weight of the component a) and per $m^2/g$ of specific surface area of the component a) means that the proportion by weight of the component b) to be used depends on the specific surface area of the component a). Thus, for example, at a specific surface area of the component a) of 10 $m^2/g$ the proportion of the component b) is from 1 to 15% by weight, based on the weight of the component a).

$TiO_2$ is suitable in both the rutile and anatase forms and mixtures thereof. As component a), preference is given to titanium dioxide having a BET surface area of from 20 to 400 $m^2/g$, preferably from 70 to 300 $m^2/g$. If mixtures of titanium dioxide with zirconium dioxide or tin dioxide are used, from 5 to 95% by weight, preferably from 5 to 50% by weight, of the titanium dioxide can be replaced by zirconium dioxide, aluminium oxide or tin dioxide.

As additional component a), one or more oxides of the metals selected from the group consisting of hafnium, niobium, tungsten, lanthanum and cerium may also be present. If the component a) is doped with the oxides mentioned, they are generally present in an amount of from 1 to 15% by weight, based on the total weight of the component a).

The proportion of the component b) is preferably from 0.1 to 0.5% by weight, particularly preferably from 0.1 to 0.2% by weight, in each case based on the weight of the component a) and per $m^2/g$ of specific surface area of the component a).

In the component b), part of the vanadium pentoxide, preferably from 10 to 90%, can, if desired, be replaced by one or more oxides of molybdenum, chromium and antimony. If desired, one or more oxides of alkali metals, elements of main groups V and VI of the Periodic Table of the Elements and the transition metals may also be present as additional component b). Examples are the oxides of lithium, sodium, potassium, rubidium, caesium, phosphorus, bismuth, sulphur, selenium, tellurium, manganese, iron, cobalt, palladium, copper, silver, gold, zinc and cadmium. In general, the amount of these dopants is from 0.05 to 15% by weight, calculated as oxides and based on the total weight of the component b). The proportion of alkali metal oxides and noble metal oxides is preferably from 0.05 to 1.0% by weight.

Preference is given to compositions having a high surface area of the component a) of from 70 to 300 m²/g, in which, if desired, tin oxide or tungsten oxide may also be present, and containing a component b) which is doped with Mo, Cr, Sb and/or Au.

The catalytically active mixed oxide composition may, if desired, additionally contain from 10 to 50% by weight, based on the total weight of the catalytically active mixed oxide composition, of inert diluents such as silicon dioxide and silicon carbide.

The catalytically active mixed oxide composition is applied as a shell to the outer surface of the support body in an amount of from 1 to 40% by weight, preferably from 5 to 25% by weight, in each case based on the total weight of support body and active composition. The thickness of the layer is generally from 10 to 1000 µm, preferably from 100 to 500 µm. The coated catalyst can also contain a plurality of layers which differ in composition. One or more constituents of the active components a) and b) can also be present in different concentrations in the individual layers.

In general, the catalytically active mixed oxide composition is applied in one layer. To influence the catalyst activity and to improve the adhesion to the support body, two or more layers can also be applied.

Preferred embodiments having a plurality of layers are those in which the inner layer contains only component a) and the outer layer contains the components a) and b). Preferred multilayer embodiments also include those in which the inner and outer layers each contain the components a) and b), where the specific surface area selected for the component a) is preferably higher for the inner layer than for the outer layer.

Suitable materials for the inert, nonporous support body are all nonporous materials which are inert under the operating conditions of the gas-phase oxidation and are stable over the operating time. Examples are steatite, duranite, silicon carbide, magnesium oxide, silicon oxide, silicates, aluminates, metals such as stainless steel and also, if desired, mixtures of these materials. Preference is given to a ceramic material such as steatite.

The support body is nonporous, which for the purposes of the present invention means that the BET surface area of the support body is <1 m²/g and the porosity is <0.1, where porosity=[1–(density of shaped body/density of substance)].

The inert, nonporous support body can have any shape. Examples of suitable shapes are spheres, cylinders, cuboids, tori, saddles, spindles and helices. The basic bodies can also have one or more recesses such as depressions, grooves or holes, and also protruding parts such as studs, points and ridges. Further examples are rings, ring segments, rings with a web, spheres with a hole and segments of spheres. Likewise suitable as supports are ordered packings such as monoliths or cross-channel structures. Preference is given to support shapes having a very high geometric surface area per volume, for example rings.

The dimensions of the support bodies are determined by the reactors for gas-phase oxidation. In general, the shaped bodies have a length or a diameter of from 2 to 20 mm. The wall thickness, for example in the case of rings or hollow cylinders, is advantageously from 0.1 to 4 mm.

To prepare the coated catalysts, the catalytically active mixed oxide composition is applied to the support body in a known way, for example by coating the support with an aqueous slurry in a rotary tube furnace or by drum coating.

It is advantageous to provide the premix of the active composition with a binder which remains in the active layer after application in order to improve its mechanical stability. It is particularly advantageous to mix the aqueous suspension of the active components with an aqueous copolymer dispersion, preferably of vinyl acetate/vinyl laurate, in an amount of from 5 to 40% by weight, based on the solids content of the dispersion and the sum of the dry weights of active composition and dispersion, and to apply this mixture to the inert, nonporous support bodies in a spray-drying step.

Repeating this step using further spray suspensions of a different composition makes it possible to prepare catalysts having a layer structure of the active catalyst shell. If one or more components of the active composition are introduced during the application procedure in amounts which change over time, catalytically active layers which have a continuous change in the composition along the thickness axis are obtained.

The invention further provides a process for preparing acetic acid by gas-phase oxidation of unsaturated $C_4$-hydrocarbons using the coated catalyst. For this purpose, a gas mixture containing oxygen or an oxygen-containing gas, preferably air, one or more $C_4$-hydrocarbons, preferably butene, water vapour and, if desired, an inert gas is reacted over the coated catalyst at elevated temperature.

The gas-phase oxidation is carried out in cooled tube reactors which are charged with the coated catalyst and through which the reaction mixture flows. Customary fixed-bed reactors are upright tube-bundle reactors having tube lengths of from 1 m to 10 m, an internal tube diameter of from 10 to 35 mm and a wall thickness of from 1 to 4 mm. Heat-exchange media suitable for cooling are particularly water, heat-transfer fluids and eutectic salt melts (e.g. $KNO_3/NaNO_2$).

The reaction tubes can, if desired, be charged with coated catalysts of different shape and dimensions and also different compositions of the active components or layers. The coated catalysts can be introduced into the reaction tubes as a random mixture or in zones.

Suitable starting materials are unsaturated hydrocarbons having four carbon atoms or gas mixtures containing hydrocarbons having four carbon atoms. Butenes give higher yields than butadienes. Preference is given to butene isomers, particularly preferably 1-butene, 2-butenes and mixtures thereof.

An advantage of the process of the invention for the gas-phase oxidation of unsaturated $C_4$-hydrocarbons using the coated catalyst is that it is also possible to use gas mixtures which contain compounds which do not react, or react only to a slight extent or in poor yields, to give acetic acid. Thus, it is also possible to use cheaper raw material mixtures from refineries, for example "$C_4$ fraction" (predominantly butadiene and i-butene), "raffinate 2 " (predominantly i-butene), "raffinate 2 " (predominantly 1-butene and 2-butenes) as starting material. The raw material mixtures mentioned can, if desired, also be subjected to a hydrogenation or purification step before use.

The reaction temperature for the oxidation of the butene/oxygen (air)/water vapour reaction mixtures is generally from 100° C. to 400° C., preferably from 150° C. to 300° C. The reaction can be carried out at the built-up pressure resulting from flow through the catalyst bed or under increased pressure. Preference is given to carrying out the reaction at a gauge pressure of from 0.2 to 30 bar.

The volume mixing ratio of butene(mixture)/oxygen(air) is generally from 0.2/99.5 to 15/85, preferably from 1/99 to 5/95. The volume mixing ratio of butene(mixture)/water vapour is generally from 1/1 to 1/50, preferably from 1/5 to 1/25. The space velocity of the gas mixture in the reactor is from 400 to 10000 $h^{-1}$, preferably from 600 to 6000 $h^{-1}$ (stp).

After the reaction, the acetic acid formed is separated off by cooling and precipitation or by absorption in a suitable solvent. The acetic acid which has been separated off is further purified by suitable methods, for example distillation or extraction. The waste gas can be recirculated.

The following examples illustrate the invention without restricting it.

CATALYST PREPARATION

The catalysts were prepared, in the amounts indicated in the examples, by milling the active components with additional water, subsequent addition of a copolymer dispersion of vinyl acetate and vinyl laurate having a solids content of 50% by weight and spraying the finished suspension, with evaporation of the water, onto 1000 g of steatite balls (4 mm diameter, BET surface area <0.01, porosity <0.01).

TESTING OF THE CATALYSTS

The catalysts were introduced into a reaction tube having an internal diameter of 12.5 mm. The tube was cooled from the outside by forced circulation of a salt melt. Unless otherwise indicated, all reactions were carried out at a gauge pressure of $1\times10^5$ Pa.

The reactor was charged with the amount of catalyst indicated in the examples (fill height=1400 mm). Unless otherwise indicated in the examples, the catalyst was heat treated in the reaction tube for 6 hours at 410° C. and an air flow of 220 standard 1/h prior to operation. The reaction gas comprised, unless otherwise indicated, 80 standard 1/h of air, 0.81 standard 1/h of 1-butene and 16.2 standard 1/h of steam. The yield is determined using the following equation: Acetic acid yield [% by weight]=(kg of acetic acid separated out/kg of starting material used)×100

The catalyst compositions and also the test conditions and test results are summarized in Table 1.

EXAMPLE 1

(Two-coat catalyst)

1st spray suspension: 70.42 g of titanium dioxide (>70% anatase modification) having a BET surface area of 48 $m^2/g$ were milled with 7.43 g of titanium dioxide (100% anatase modification, BET=8 $m^2/g$), 14.67 g of $V_2O_5$ and 900 ml of deionized water for 20 hours in a ball mill. 29 g of a copolymer dispersion of vinyl acetate and vinyl laurate having a solids content of 50% by weight were then added to the homogeneous suspension and the mixture was intimately mixed by stirring. 2nd spray suspension: 5 g of titanium dioxide (100% anatase modification, BET=8 $m^2/g$), 3 g of a copolymer dispersion of vinyl acetate/vinyl laurate having a solids content of 50% by weight and 100 ml of deionized water were intimately mixed by stirring. The 2 nd spray suspension was first applied to 1000 g of 4 mm steatite balls and dried. The 1st spray suspension was then applied and dried. 202 g of catalyst were placed in the reactor (fill height=1400 mm). At a salt bath temperature of 213.5° C., a conversion of 88.6% was achieved and the acetic acid yield was 116.25% by weight.

EXAMPLE 2

(One-coat catalyst, low surface area)

211 g of titanium dioxide (>70% anatase modification) having a BET surface area of 48 $m^2/g$ were milled with 44 g of $V_2O_5$ and 1500 ml of deionized water for 20 hours in a ball mill and, after addition of the binder, applied to the steatite balls. 200 g of catalyst were placed in the reactor (fill height=1400 mm). At a salt bath temperature of 198° C., a conversion of 88% was achieved and the acetic acid yield was 116.5% by weight.

EXAMPLE 3

(High proportion of water vapour)

The procedure of Example 2 was repeated, except that the reaction gas comprised 100 standard 1/h of air, 1.01 standard 1/h of 1-butene and 50.5 standard 1/h of steam. At a salt bath temperature of 197° C., a conversion of 75% was achieved and the acetic acid yield was 103% by weight.

EXAMPLE 4

(High layer thickness)

297.1 g of titanium dioxide (>70% anatase modification) having a BET surface area of 48 $m^2/g$ were milled with 51.3 g of $V_2O_5$ and 1500 ml of deionized water for 19 hours in a ball mill and, after addition of the binder, applied to the steatite balls. 177 g of catalyst were placed in the reactor (fill height=1400 mm). The reaction gas contained 24.8 standard 1/h of steam. At a salt bath temperature of 196° C., a conversion of 95% was achieved and the acetic acid yield was 113.5% by weight.

EXAMPLE 5

(High vanadium content)

135 g of titanium dioxide (anatase modification) having a BET surface area of 75 $m^2/g$ were milled with 120 g of $V_2O_5$ and 1400 ml of deionized water for 24 hours in a ball mill and, after addition of the binder, applied to the steatite balls. 168 g of catalyst were placed in the reactor (fill height=1400 mm). The reaction gas contained 24.8 standard 1/h of steam. At a salt bath temperature of 189° C., a conversion of 92% was achieved and the acetic acid yield was 105% by weight.

EXAMPLE 6

(Tungsten doping)

186.2 g of titanium dioxide (anatase modification with 10% by weight of $WO_3$) having a BET surface area of 75 $m^2/g$ were milled with 68.9 g of $V_2O_5$ and 700 ml of deionized water for 120 hours in a ball mill and, after addition of the binder, applied to the steatite balls. 192 g of catalyst were placed in the reactor (fill height=1400 mm). At a salt bath temperature of 179° C., a conversion of 95% was achieved, the hot spot temperature was 190° C. and the acetic acid yield was 116.2% by weight.

EXAMPLE 7

(Low $C_4$ concentration)

The procedure of EXAMPLE 5 was repeated, except that the reaction gas comprised 206 standard 1/h of air, 0.62 standard 1/h of 1-butene and 42 standard 1/h of steam. At a salt bath temperature of 192.5° C., a conversion of 96% was achieved and the acetic acid yield was 128.1% by weight.

EXAMPLE 8

(One-coat catalyst having a very high surface area)

186.37 g of titanium dioxide (anatase modification) having a BET surface area of 250 $m^2/g$ were milled with 68 g of $V_2O_5$ and 1500 ml of deionized water for 18 hours in a ball mill and, after addition of the binder, applied to the steatite balls. 25 153.4 g of catalyst were placed in the reactor (fill height=1400 mm). At a salt bath temperature of 174° C., a conversion of 96.2% was achieved, and the acetic acid yield was 133% by weight.

EXAMPLE 9

(Caesium/phosphorus doping)

217.5 g of titanium dioxide (>70% anatase modification) having a BET surface area of 48 $m^2/g$ were milled with 37.6 g of $V_2O_5$, 1.6 g of caesium carbonate, 4.8 g.of ammonium dihydrogen phosphate and 1000 ml of deionized water for 48 hours in a ball mill and, after addition of the binder, applied to the steatite balls. 166.8 g of catalyst were placed in the reactor (fill height=1400 mm). At a salt bath temperature of 221.5° C., a conversion of 94% was achieved, the hot spot temperature was 223° C. and the acetic acid yield was 105.5% by weight.

EXAMPLE 10

(Molybdenum doping)

219.98 g of titanium dioxide (anatase modification) having a BET surface area of 44.4 $m^2/g$ were milled with 31.33 g of $V_2O_5$, 6.25 g of molybdenum trioxide and 1000 ml of deionized water for 22 hours in a ball mill and, after addition of the binder, applied to the steatite balls. 167 g of catalyst were placed in the reactor (fill height=1400 mm). At a salt bath temperature of 194° C., a conversion of 93% was achieved, and the acetic acid yield was 112.4% by weight.

EXAMPLE 11

(Two-coat catalyst)

1st spray suspension: 101.65 g of titanium dioxide (100% anatase modification) having a BET surface area of 75 $m^2/g$ were milled with 27.1 g of $V_2O_5$ and 500 ml of deionized water for 20 hours in a ball mill. 43.50 g of a copolymer dispersion of vinyl acetate and vinyl laurate having a solids content of 50% by weight were then added to the homogeneous suspension and the mixture was intimately mixed by stirring. 2nd spray suspension: 122.6 g of titanium dioxide (100% anatase modification, BET=17 $m^2/g$), 7.50 g of vanadium pentoxide and 500 ml of deionized water were milled for 20 hours in a ball mill. 43.49 g of a copolymer dispersion of vinyl acetate and vinyl laurate having a solids content of 50% by weight were then added to the homogeneous suspension and the mixture was intimately mixed by stirring. The 1st spray suspension was first applied to 1000 g of 4 mm steatite balls. The 2nd spray suspension was then applied. 167 g of catalyst were placed in the reactor (fill height=1400 mm). At a salt bath temperature of 185° C., a conversion of 92% was achieved and the acetic acid yield was 116% by weight.

EXAMPLE 12

(Mo/Na doping)

100.0 g of titanium dioxide (100% anatase modification) having a BET surface area of 15 $m^2/g$ were milled with 5.32 g of $V_2O_5$, 1.065 g of molybdenum trioxide, 0.245 g of sodium carbonate and 1000 ml of deionized water for 20 hours in a ball mill and, after addition of the binder, applied to the steatite balls. 202 g of catalyst were placed in the reactor (fill height=1400 mm). At a salt bath temperature of 252° C., a conversion of 92% was achieved, and the acetic acid yield was 96.4% by weight.

EXAMPLE 13

(Low vanadium content)

225 g of titanium dioxide (100% anatase modification) having a BET surface area of 75 $m^2/g$ were milled with 30 g of $V_2O_5$ and 1500 ml of deionized water for 35 hours in a ball mill and, after addition of the binder, applied to 1000 g of 4 mm steatite balls. 158 g of catalyst were placed in the reactor (fill height=1400 mm). At a salt bath temperature of 179° C., a conversion of 95% was achieved and the acetic acid yield was 121.3% by weight.

EXAMPLE 14

(Sulphur doping)

188 g of titanium dioxide (anatase modification) having a BET surface area of 140 $m^2/g$ and a sulphate content of 4.6% by weight were milled with 69 g of $V_2O_5$ and 1500 ml of deionized water for 100 hours in a ball mill and, after addition of the binder, applied to the steatite balls. 161 g of catalyst were placed in the reactor (fill height=1400 mm). At a salt bath temperature of 172.5° C., a conversion of 95% was achieved and the acetic acid yield was 130% by weight.

EXAMPLE 15

(High Mo content)

225 g of titanium dioxide (anatase modification) having a BET surface area of 75 $m^2/g$ were milled with 10 g of $V_2O_5$, 20 g of $MoO_3$ and 1500 ml of deionized water for 68 hours in a ball mill and, after addition of the binder, applied to the steatite balls. 162 g of catalyst were placed in the reactor (fill height=1400 mm). At a salt bath temperature of 183.5° C., a conversion of 94.5% was achieved and the acetic acid yield was 120% by weight.

EXAMPLE 16

(Antimony doping)

225 g of titanium dioxide (anatase modification) having a BET surface area of 75 $m^2/g$ were milled with 26.3 g of $V_2O_5$, 10.5 g of $Sb_2O_3$ and 2000 ml of deionized water for 24 hours in a ball mill and, after addition of the binder, applied to the steatite balls. 166 g of catalyst were placed in the reactor (fill height=1400 mm). At a salt bath temperature of 175° C., a conversion of 94.4% was achieved and the acetic acid yield was 142% by weight.

EXAMPLE 17

(Bismuth doping)

225 g of titanium dioxide (100% anatase modification) having a BET surface area of 75 $m^2/g$ were milled with 26.3 g of $V_2O_5$, 10.5 g of $Bi_2O_3$ and 1500 ml of deionized water for 48 hours in a ball mill and, after addition of the binder, applied to the steatite balls. 151 g of catalyst were placed in the reactor (fill height=1400 mm). At a salt bath temperature of 179° C., a conversion of 90.2% was achieved and the acetic acid yield was 120% by weight.

EXAMPLE 18

(Tellurium doping)

225 g of titanium dioxide (100% anatase modification) having a BET surface area of 75 $m^2/g$ were milled with 26.3 g of $V_2O_5$, 10.5 g of $TeO_2$ and 2000 ml of deionized water for 47 hours in a ball mill and, after addition of the binder, applied to the steatite balls. 159 g of catalyst were placed in the reactor (fill height=1400 mm). At a salt bath temperature of 203° C., a conversion of 88% was achieved and the acetic acid yield was 103% by weight.

EXAMPLE 19

(Manganese doping)

225 g of titanium dioxide (100% anatase modification) having a BET surface area of 75 $m^2/g$ were milled with 26.3 g of $V_2O_5$, 10.5 g of $MnO_2$ and 1500 ml of deionized water for 19 hours in a ball mill and, after addition of the binder, applied to the steatite balls. 158 g of catalyst were placed in the reactor (fill height=1400 mm). At a salt bath temperature of 194° C., a conversion of 90% was achieved and the acetic acid yield was 111.3% by weight.

EXAMPLE 20

(Copper doping)

225 g of titanium dioxide (100% anatase modification) having a BET surface area of 75 $m^2/g$ were milled with 26.3 g of $V_2O_5$, 1.42 g of $Cu(NO_3)_2 \cdot 3H_2O$ and 1200 ml of deionized water for 19 hours in a ball mill and, after addition of the binder, applied to the steatite balls. 159 g of catalyst were placed in the reactor (fill height=1400 mm). At a salt bath temperature of 180° C., a conversion of 94% was achieved and the acetic acid yield was 120% by weight.

EXAMPLE 21

(Zinc doping)

225 g of titanium dioxide (100% anatase modification) having a BET surface area of 75 $m^2/g$ were milled with 26.3 g of $V_2O_5$, 1.11 g of zinc(II) acetate dihydrate and 1500 ml of deionized water for 43 hours in a ball mill and, after addition of the binder, applied to the steatite balls. 157 g of catalyst were placed in the reactor (fill height=1400 mm). At a salt bath temperature of 178.5° C., a conversion of 94.6% was achieved and the acetic acid yield was 124.2% by weight.

EXAMPLE 22

(Gold doping)

225 g of titanium dioxide (100% anatase modification) having a BET surface area of 75 $m^2/g$ were milled with 26.3 g of $V_2O_5$, 0.94 g of tetrachloroauric acid and 1500 ml of deionized water for 46 hours in a ball mill and, after addition of the binder, applied to the steatite balls. 162 g of catalyst were placed in the reactor (fill height=1400 mm). At a salt bath temperature of 182° C., a conversion of 95.8% was achieved and the acetic acid yield was 128.4% by weight.

EXAMPLE 23

(Chromium doping)

225 g of titanium dioxide (100% anatase modification) having a BET surface area of 75 $m^2/g$ were milled with 24 g of $V_2O_5$, 2.9 g of chromium trioxide and 1500 ml of deionized water for 22 hours in a ball mill and, after addition of the binder, applied to the steatite balls. 174.8 g of catalyst were placed in the reactor (fill height=1400 mm). At a salt bath temperature of 184° C., a conversion of 95% was achieved and the acetic acid yield was 128% by weight.

EXAMPLE 24

(Ti/Sn catalyst)

200 g of titanium dioxide (100% anatase modification) having a BET surface area of 75 $m^2/g$ were milled with 70 g of tin tetrachloride pentahydrate, 26.3 g of $V_2O_5$ and 1500 ml of deionized water for 46 hours in a ball mill and, after addition of the binder, applied to the steatite balls. 160.1 g of catalyst were placed in the reactor (fill height=1400 mm). At a salt bath temperature of 191° C., a conversion of 94% was achieved and the acetic acid yield was 130% by weight.

EXAMPLE 25

(Ti/Zr catalyst)

171 g of a Ti/Zr mixed oxide (9% by weight of $ZrO_2$) prepared by a sol-gel process and having a BET surface area of 75 $m^2/g$ were milled with 15.2 g of $V_2O_5$, 3.8 g of $MoO_3$, 9.1 g of $Sb_2O_3$ and 1000 ml of deionized water for 14 hours in a ball mill and, after addition of the binder, applied to 760 g of the steatite balls. 162.4 g of catalyst were placed in the reactor (fill height=1400 mm). At a salt bath temperature of 201° C., a conversion of 93% was achieved and the acetic acid yield was 112% by weight.

EXAMPLE 26

(Ti/Zr catalyst)

171 g of a Ti/Zr mixed oxide (9% by weight of $ZrO_2$) prepared by a sol-gel process and having a BET surface area of 110 $m^2/g$ were milled with 36.8 g of $V_2O_5$, 9.2 g of $MoO_3$, 21.3 g of $Sb_2O_3$ and 1000 ml of deionized water for 14 hours in a ball mill and, after addition of the binder, applied to 760 g of the steatite balls. 155.5 g of catalyst were placed in the reactor (fill height=1400 mm). At a salt bath temperature of 199° C., a conversion of 95% was achieved and the acetic acid yield was 115% by weight.

EXAMPLE 27

(Niobium doping)

151 g of a Ti/Nb mixed oxide (9% by weight of $Nb_2O_5$) prepared by a sol-gel process and having a BET surface area of 70 $m^2/g$ were milled with 14.5 g of $V_2O_5$, 3.6 g of $MoO_3$, 8.7 g of $Sb_2O_3$ and 800 ml of deionized water for 14 hours in a ball mill and, after addition of the binder, applied to 700 g of the steatite balls. 169.5 g of catalyst were placed in the reactor (fill height=1400 mm). At a salt bath temperature of 219° C., a conversion of 96% was achieved and the acetic acid yield was 105% by weight.

COMPARATIVE EXAMPLE 1

(Uniform-composition catalyst)

200 g of titanium dioxide (100% anatase modification) having a BET surface area of 8 $m^2/g$ were mixed with 8.1 g of $V_2O_5$ and 10 g of graphite, milled, sieved and pressed to form cylindrical pellets (4×4 mm). 155 g of catalyst were placed in the reactor (fill height=1400 mm). At a salt bath temperature of 247° C., a conversion of 90% was achieved and the acetic acid yield was 77% by weight.

COMPARATIVE EXAMPLE 2

(DE-A 2235103)

A porous (porosity=0.65) alpha-aluminium oxide support (irregular crushed material) was impregnated under reduced pressure with a hydrochloric acid-containing vanadium/titanium solution prepared as described for the example catalyst 1 in DE-A 2235103 and then dried and calcined as described in this example. 134.5 g of the catalyst screened to 4 mm were placed in the reactor (fill height=1400 mm). At a salt bath temperature of 200° C., a butene conversion of 96% was achieved but the acetic acid yield was only 94%. This catalyst gave significantly more by-products (maleic acid, propionic acid).

TABLE 1

| Ex. | Catalyst | Reaction conditions | Temperature [° C.] | Conversion [%] | Yield [%] |
|---|---|---|---|---|---|
| 1 | 2 coats | standard | 213.5 | 88.6 | 116.25 |
| 2 | low surface area | standard | 198 | 88.0 | 116.5 |
| 3 | low surface area | large amount of steam | 197 | 75.0 | 103.0 |
| 4 | thick layer | large amount of steam | 196 | 95.0 | 113.5 |
| 5 | high V content | large amount of steam | 189 | 92.0 | 105.0 |
| 6 | W doping | standard | 179 | 95.0 | 116.2 |
| 7 | small amount of C4 | small amount of butene | 192.5 | 96.0 | 128.1 |
| 8 | high surface area | standard | 174 | 96.2 | 133.0 |
| 9 | Cs/P doping | standard | 221.5 | 94.0 | 105.5 |
| 10 | Mo doping | standard | 194 | 93.0 | 112.4 |
| 11 | 2 coats | standard | 185 | 92.0 | 116.0 |
| 12 | Mo/Na doping | standard | 252 | 92.0 | 96.4 |
| 13 | low vanadium content | standard | 179 | 95.0 | 121.3 |
| 14 | S doping | standard | 172.5 | 95.0 | 130.0 |
| 15 | high Mo content | standard | 183.5 | 94.5 | 120.0 |
| 16 | Sb doping | standard | 175 | 94.4 | 142.0 |
| 17 | Bi doping | standard | 179 | 90.2 | 120.0 |
| 18 | Te doping | standard | 203 | 88.0 | 103.0 |
| 18 | Mn doping | standard | 194 | 90.0 | 111.3 |
| 20 | Cu doping | standard | 180 | 94.0 | 120.0 |
| 21 | Zn doping | standard | 178.5 | 94.6 | 124.2 |
| 22 | Au doping | standard | 182 | 95.8 | 128.4 |
| 23 | Cr doping | standard | 184 | 95.0 | 128.0 |
| 24 | Ti/Sn catalyst | standard | 191 | 94.0 | 130.0 |
| 25 | Ti/Zr catalyst | standard | 201 | 93.0 | 112.0 |
| 26 | Ti/Zr catalyst | standard | 199 | 95.0 | 115.0 |
| 27 | Nb doping | standard | 219 | 96.0 | 105.0 |
| C1 | uniform-composition catalyst | standard | 247 | 90.0 | 77.0 |
| C2 | DE-A 2235103 | standard | 200 | 96.0 | 94.0 |

What is claimed is:

1. Coated catalyst for preparing acetic acid by gas-phase oxidation of unsaturated $C_4$-hydrocarbons comprising an inert nonporous support body and a catalytically active mixed-oxide composition which is applied to an outer surface of the support body and contains
   a) at least one oxide selected from the group consisting of titanium dioxide, zirconium dioxide, tin dioxide, and aluminum oxide; and
   b) from 0.1% to 1.5% by weight, based on the weight of the component a) and per $m^2/g$ of specific surface area of the component a), of vanadium pentoxide.

2. The coated catalyst according to claim 1, wherein the catalytically active mixed oxide composition is applied to the outer surface of the support body in an amount of from 1% to 40% by weight, based on the total weight of support body and active composition, as a shell having a layer thickness of from 10 to 1000 µm.

3. The coated catalyst according to claim 1, wherein the coated catalyst contains at least one layer of the catalytically active mixed oxide composition.

4. The coated catalyst according to claim 3, wherein the coated catalyst contains a plurality of layers, where an inner layer contains only component a) and an outer layer contains the components a) and b).

5. The coated catalyst according to claim 3, wherein the coated catalyst contains a plurality of layers, where an inner layer and an outer layer each contains the components a) and b) and the specific surface area selected for the component a) is higher for the inner layer than for the outer layer.

6. Process for preparing acetic acid by gas-phase oxidation of unsaturated $C_4$-hydrocarbons in a tube reactor comprising using a coated catalyst which comprises an inert nonporous support body and a catalytically active mixed oxide composition which is applied to an outer surface of the support body and contains
   a) at least one oxide selected from the group consisting of titanium dioxide, zirconium dioxide, tin dioxide, and aluminum oxide; and
   b) from 0.1% to 1.5% by weight, based on the weight of the component a) and per $m^2/g$ of specific surface area of the component a), of vanadium pentoxide; and reacting a gas mixture containing oxygen or oxygen-containing gas, one or more $C_4$-hydrocarbons and water vapour and having a volume mixing ratio of butene (mixture)/oxygen (air) of from 0.2/99.5 to 15/85 and a volume mixing ratio of butene (mixture)/water vapour of from 1/1 to 1/50 by contacting the coated catalyst at a temperature of from 100° C. to 400° C. and a gauge pressure of from 0.2 to 30 bar.

7. Process for preparing acetic acid by gas-phase oxidation of unsaturated $C_4$-hydrocarbons in a tube reactor according to claim 6 comprising introducing said coated catalyst into zones in reaction tubes of said tube reactor.
   (a) at least one oxide selected from the group consisting of titanium dioxide, zirconium dioxide, tin dioxide, and aluminum oxide; and wherein component (a) additionally contains at least one oxide of a metal selected from the group consisting of hafnium, niobium, lanthanum and cerium in an amount of from 1% to 15% by weight, based on the total weight of the component (a); and
   (b) from 0.1% to 1.5% by weight, based on the weight of the component (a) of vanadium pentoxide; and reacting a gas mixture containing oxygen or oxygen-containing gas, one or more $C_4$-hydrocarbons consisting of unsaturated C4-hydrocarbons and water vapour and having a volume mixing ratio of butene (mixture)/oxygen (air) of from 0.2/99.5 to 15/85 and a volume mixing ratio of butene (mixture)/water vapour of from 1/1 to 1/50 by contacting the coated catalyst at a temperature of from 100° C. to 400° C. and a gauge pressure of from 0.2 to 30 bar.

8. Coated catalyst for preparing acetic acid by gas-phase oxidation of unsaturated C4-hydrocarbons comprising an inert nonporous support body and a catalytically active mixed oxide composition which is applied to an outer surface of the support body and contains (a) at least one oxide selected from the group consisting of titanium dioxide, zirconium dioxide, tin dioxide, and aluminum oxide; and wherein component (a) additionally contains at least one oxide of a metal selected from the group consisting of hafnium, niobium, lanthanum and cerium in an amount of from 1% to 15% by weight, based on the total weight of the component (a); and (b) from 0.1% to 1.5% by weight, based on the weight of the component (a) of vanadium pentoxide; and wherein component (b) additionally has part of the vanadium pentoxide being replaced by at least one oxide of a metal selected from the group consisting of molybdenum, chromium, antimony, at least one oxide of an alkali metal, elements of main group groups V and VI of the Periodic Table of the Elements, and a transition metal which is present as an additional component (b).

\* \* \* \* \*